US006533978B1

(12) United States Patent
Wisneski et al.

(10) Patent No.: US 6,533,978 B1
(45) Date of Patent: *Mar. 18, 2003

(54) PROCESS AND APPARATUS FOR FORMING A STABILIZED ABSORBENT WEB

(75) Inventors: Anthony John Wisneski, Kimberly, WI (US); Yong Li, Appleton, WI (US); Michael Franklin Kalmon, Atoka, TN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 281 days.

This patent is subject to a terminal disclaimer.

(21) Appl. No.: 09/631,492

(22) Filed: Aug. 3, 2000

(51) Int. Cl.$^7$ ............................. B27N 3/04; A61F 13/15
(52) U.S. Cl. ........................................ 264/113; 425/81.1
(58) Field of Search .................................. 264/510, 518, 264/113; 425/81.1, 83.1

(56) References Cited

U.S. PATENT DOCUMENTS

| | | |
|---|---|---|
| 2,757,150 A | 7/1956 | Heritage |
| 3,082,138 A | 3/1963 | Hjelt |
| 3,453,355 A | 7/1969 | Rudloff |

(List continued on next page.)

FOREIGN PATENT DOCUMENTS

| | | |
|---|---|---|
| EP | 0 217 032 A2 | 4/1987 |
| EP | 0 427 316 A2 | 5/1991 |
| EP | 0 427 317 A2 | 5/1991 |
| EP | 0 429 112 A2 | 5/1991 |
| EP | 0 440 472 B1 | 8/1995 |
| GB | 1251753 | 10/1971 |
| GB | 1356100 | 6/1974 |
| GB | 2015604 A | 9/1979 |
| WO | WO 92/07985 A1 | 5/1992 |
| WO | WO 94/04351 | 3/1994 |
| WO | WO 94/04352 | 3/1994 |
| WO | WO 95/16425 | 6/1995 |
| WO | WO 96/06223 A1 | 2/1996 |
| WO | WO 98/20821 A1 | 5/1998 |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

*Primary Examiner*—Mary Lynn Theisen
(74) *Attorney, Agent, or Firm*—Paul Yee; Thomas M. Parker

(57) ABSTRACT

An apparatus and process for forming an absorbent web (26) includes an airlaying of a first fibrous stratum (28) which has a first quantity of absorbent fibers; an airlaying of a second fibrous stratum (34) which has a second quantity of absorbent fibers; and an airlaying of a third, intermediate fibrous stratum (40) which has a third quantity of absorbent fibers. The intermediate fibrous stratum has a location that is interposed between the first fibrous stratum and the second fibrous stratum. A liquid, wet-strength agent is distributed onto the fibers of the intermediate fibrous stratum (40) during the airlaying of the intermediate fibrous stratum to thereby render the intermediate fibrous stratum substantially non-dispersible. The process and apparatus are configured to operatively form or join the intermediate fibrous stratum (40) with at least the first fibrous stratum (28), and in desired aspects, the invention can integrally form or join the intermediate fibrous stratum (40) with both of the first and second fibrous strata (28) and (34), respectively. In a particular aspect, the invention can configure the first and second fibrous strata (28) and (34) to be substantially dispersible in an aqueous liquid, and in a further aspect, the composite strata of the web (26) can be operatively compressed prior to a curing of the wet-strength agent.

30 Claims, 8 Drawing Sheets

U.S. PATENT DOCUMENTS

| | | |
|---|---|---|
| 3,658,613 A | 4/1972 | Steiger |
| 3,819,470 A | 6/1974 | Shaw et al. |
| 3,901,236 A | 8/1975 | Assarsson et al. |
| 3,903,889 A | 9/1975 | Torr |
| 4,076,663 A | 2/1978 | Masuda et al. |
| 4,286,082 A | 8/1981 | Tsubakimoto et al. |
| 4,410,571 A | 10/1983 | Korpman |
| 4,412,036 A | 10/1983 | Pedersen et al. |
| 4,467,012 A | 8/1984 | Pedersen et al. |
| 4,495,119 A | 1/1985 | Chung |
| 4,543,410 A | 9/1985 | Cruz, Jr. |
| 4,551,377 A | 11/1985 | Elves et al. |
| 4,573,989 A | 3/1986 | Karami et al. |
| 4,584,357 A | 4/1986 | Harding |
| 4,600,462 A | 7/1986 | Watt |
| 4,663,220 A | 5/1987 | Wisneski et al. |
| 4,666,647 A | 5/1987 | Enloe et al. |
| 4,676,196 A | 6/1987 | Lojek et al. |
| 4,699,823 A | 10/1987 | Kellenberger et al. |
| 4,704,116 A | 11/1987 | Enloe |
| 4,753,646 A | 6/1988 | Enloe |
| 4,761,258 A | 8/1988 | Enloe |
| 4,822,453 A | 4/1989 | Dean et al. |
| 4,853,086 A | 8/1989 | Graef |
| 4,889,595 A | 12/1989 | Herron et al. |
| 4,927,582 A | 5/1990 | Bryson |
| 4,935,022 A | 6/1990 | Lash et al. |
| 4,938,753 A | 7/1990 | Van Gompel et al. |
| 4,977,892 A | 12/1990 | Ewall |
| 5,013,309 A | 5/1991 | Baigas, Jr. et al. |
| 5,015,245 A | 5/1991 | Noda |
| 5,028,224 A | 7/1991 | Pieper et al. |
| 5,064,689 A | 11/1991 | Young, Sr. et al. |
| 5,071,681 A | 12/1991 | Manning et al. |
| 5,171,237 A | 12/1992 | Poccia et al. |
| 5,188,624 A | 2/1993 | Young, Sr. et al. |
| 5,226,992 A | 7/1993 | Morman |
| 5,227,107 A | 7/1993 | Dickenson et al. |
| 5,230,959 A | 7/1993 | Young, Sr. et al. |
| 5,246,429 A | 9/1993 | Poccia et al. |
| 5,262,218 A | 11/1993 | Putzier |
| 5,300,192 A | 4/1994 | Hansen et al. |
| 5,308,896 A | 5/1994 | Hansen et al. |
| 5,350,370 A | 9/1994 | Jackson et al. |
| 5,352,480 A | 10/1994 | Hansen et al. |
| 5,360,420 A | 11/1994 | Cook et al. |
| 5,378,528 A | 1/1995 | Makoui |
| 5,399,219 A | 3/1995 | Roessler et al. |
| 5,405,501 A | 4/1995 | Phan et al. |
| 5,429,788 A | 7/1995 | Ribble et al. |
| 5,432,000 A | 7/1995 | Young, Sr. et al. |
| 5,445,777 A | 8/1995 | Noel et al. |
| 5,540,796 A | 7/1996 | Fries |
| 5,562,650 A | 10/1996 | Everett et al. |
| 5,595,618 A | 1/1997 | Fries et al. |
| 5,669,894 A | 9/1997 | Goldman et al. |
| 5,722,966 A | 3/1998 | Christon et al. |
| 5,770,528 A | 6/1998 | Mumick et al. |
| 5,904,675 A | 5/1999 | Laux et al. |
| 5,972,265 A | 10/1999 | Marra et al. |
| 5,990,377 A | 11/1999 | Chen et al. |
| 6,235,966 B1 | 5/2001 | Magnusson et al. |

PROCESS AND APPARATUS FOR FORMING A STABILIZED ABSORBENT WEB

FIELD OF THE INVENTION

The present invention relates to a technique for producing an absorbent article. More particularly, the invention relates to a method and apparatus for forming a stabilized absorbent web.

BACKGROUND OF THE INVENTION

Absorbent articles and structures, such as absorbent pads and absorbent cores, have been formed by employing various techniques, such as wet forming techniques, and air laying techniques. Conventional air laying techniques have transported a foraminous forming surface, such as a forming screen, through a forming chamber. Fibrous materials and particulate materials have been introduced into the forming chamber, and a vacuum source has been employed to draw an air stream through the forming surface. The air stream entrains the fibers and particulate material for deposition onto the moving forming surface.

Conventional distribution devices, such as nozzles, have been employed to deliver particulate material in desired regions along the thickness dimension of an airlaid fibrous web. Conventional devices have also been employed to distribute binder materials into an airlaid fibrous web. Such conventional processes and apparatus have been employed to combine binder fibers into an airlaid fibrous web, and in particular arrangements, the binder fibers have been composed of synthetic polymers.

In other conventional systems, multiple forming chambers have been employed to form different layers of material in a composite absorbent article. The different layers may be composed of different types of fibrous material, and different types of particulate material.

Conventional techniques, such as those described above, have been excessively complex and costly. When such conventional techniques have been employed to construct absorbent structures with high wet-strength, the structures have been excessively stiff, and have required the incorporation of excessive amounts of expensive materials. In addition, the resulting structures have suffered an excessive degradation in absorption properties, particularly excessive reductions in the rate of absorption. As a result, there has been a continued need for improved techniques for generating an absorbent structure having desired combinations of softness, strength and absorbency.

BRIEF DESCRIPTION OF THE INVENTION

The present invention provides a distinctive method and apparatus for forming a stabilized absorbent article. In the method aspect of the invention, a process for forming an absorbent web can include an airlaying of a first fibrous stratum which has a first quantity of absorbent fibers; an airlaying of a second fibrous stratum which has a second quantity of absorbent fibers; and an airlaying of a third, intermediate fibrous stratum which has a third quantity of absorbent fibers. The intermediate fibrous stratum is interposed between the first fibrous stratum and the second fibrous stratum, and a liquid, wet-strength agent is distributed onto the fibers of the intermediate fibrous stratum during the airlaying of the intermediate fibrous stratum to thereby render the intermediate fibrous stratum substantially non-dispersible.

Generally stated, the apparatus for forming an absorbent web includes a fiber source which can supply fibers for airlaying onto a forming surface to provide a first fibrous stratum having a first quantity of absorbent fibers, a second fibrous stratum having a second quantity of absorbent fibers, and an intermediate fibrous stratum having a third quantity of absorbent fibers. The intermediate fibrous stratum is interposed between the first fibrous stratum and the second fibrous stratum. The apparatus also includes a nozzle which can distribute a liquid, wet-strength agent onto the fibers of the intermediate fibrous stratum during the airlaying of the intermediate fibrous stratum to thereby render the intermediate fibrous stratum substantially non-dispersible in liquid.

In its various aspects and configurations, the method and apparatus of the present invention can advantageously provide an efficient and low cost technique which forms a distinctively stratified absorbent web by employing an airlaying operation. The technique can more efficiently utilize a wet-strength agent to provide a sufficiently high strength while incorporating a relatively small quantity of the wet-strength agent. Additionally, the technique can reliably and efficiently locate the wet-strength agent in an intermediate stratum to help maintain desired levels of softness in other strata of the absorbent structure. The process and apparatus of the invention can also distribute the wet-strength agent with an system that is less susceptible to clogging. As a result, the technique of the invention can more efficiently produce an absorbent structure having desired combinations of dry strength, wet strength, softness, flexibility and liquid distribution.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The present invention can provide an improved method and apparatus for forming an article having a plurality of strata which include selected distributions of fibrous material and binder material. Desired arrangements of the invention can provide a selected configuration of the fiber and binder material in each stratum, and in particular aspects, one or more selected strata can include superabsorbent material. The invention can, for example, be employed to form absorbent structures incorporated in personal care products, such as infant diapers, feminine care products, children's training pants, adult incontinence products, and the like.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

For the purposes of the present disclosure, the term "airlaying" is intended to include any operative technique which employs a movement of air, or other gas, to form a selected web or web strata composed of fibers and/or particles. Preferably, the direction of the gas movement is generally aligned with and assisted by the force of gravity. Optionally, the direction of the gas movement can be non-aligned with the force of gravity.

Figure 1:
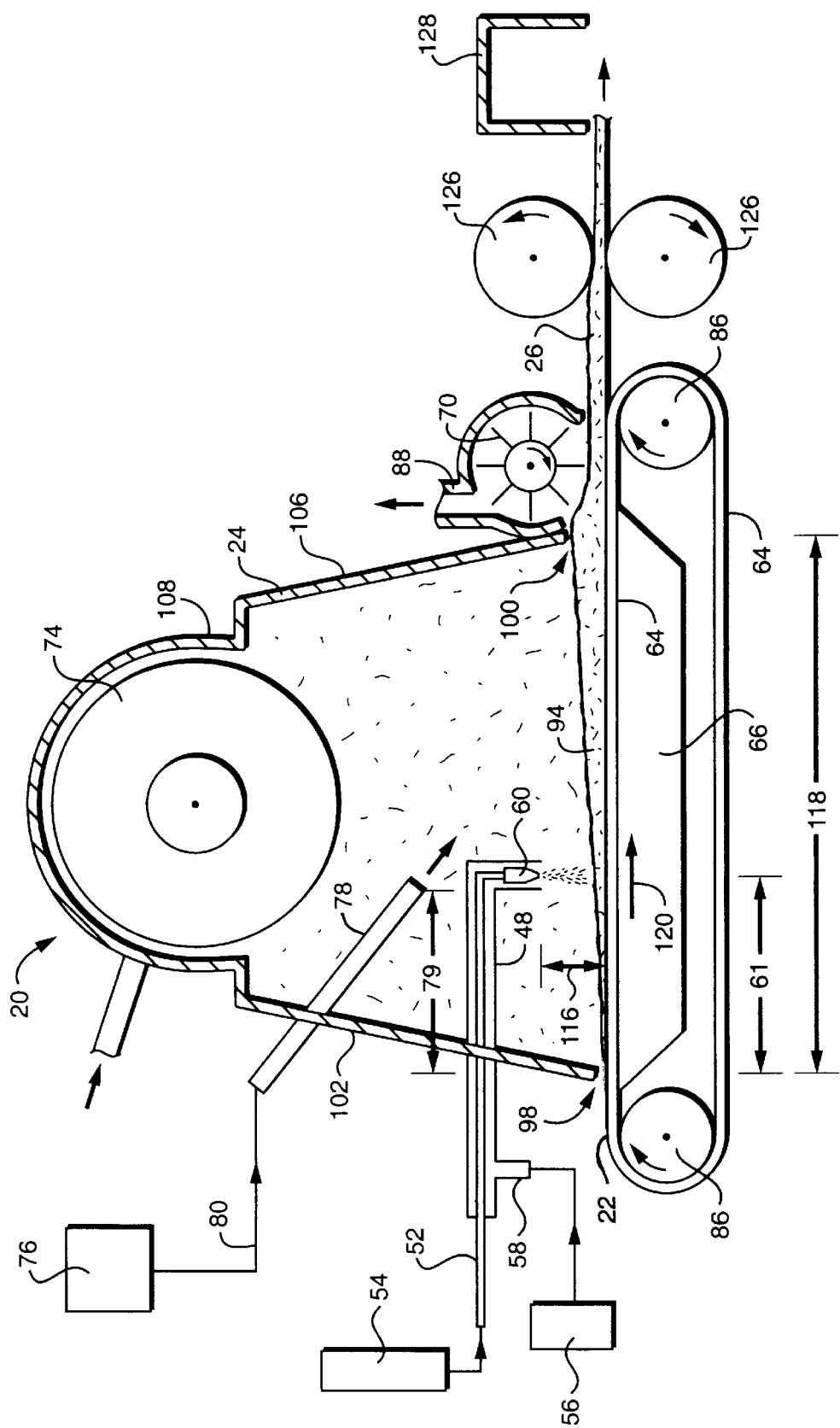
FIG. 1 representatively shows a schematic side view of a forming system of the invention which incorporates a mechanism for distributing the wet-strength agent during the airforming of the intermediate fibrous stratum.
Figure 1A:
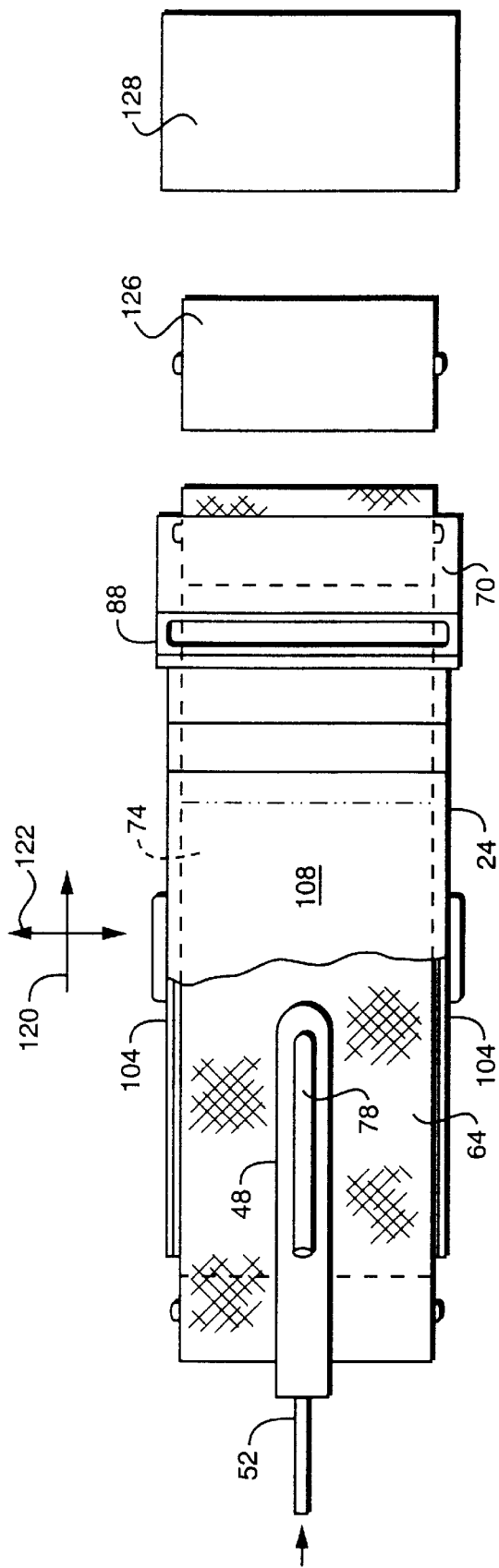
FIG. 1A representatively shows a schematic, partially cut away, top view of the forming system illustrated in FIG. 1, without the formed absorbent web.
Figure 2:
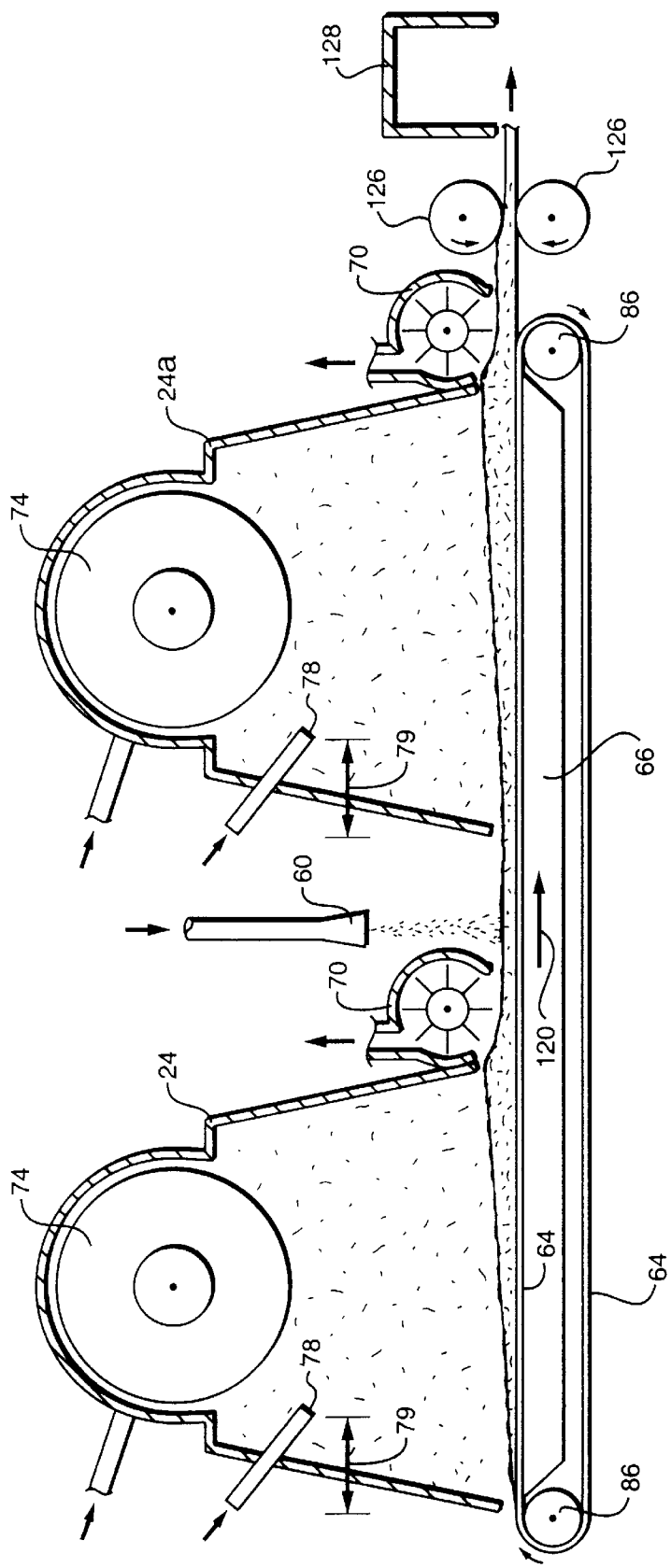
FIG. 2 representatively shows a schematic side view of an alternative, multiple chamber forming system which incorporates a mechanism for distributing the wet-strength agent onto the fibers of the intermediate fibrous stratum during an operation that is removed and separate from the airforming of the first and intermediate fibrous strata.

With reference to FIGS. 1 through 2, the process and apparatus of the invention has an appointed machine-direction 120 and an appointed cross-direction 122 (e.g. FIG. 1A). For the present disclosure, the machine-direction 120 is the direction along which a particular component or material is transported length-wise along and through a particular, local position of the apparatus and method. The cross-direction 122 lies generally within the plane of the material being transported through the process and is aligned perpendicular to the local machine-direction 120. Accordingly, in the view of the arrangement representatively shown in FIG. 1, the cross-direction 122 extends generally perpendicular to the plane of the sheet of the drawing.

In the various aspects and configurations of the invention, a suitable conveying or transport mechanism is employed to move appointed components through the method and apparatus of the invention. The transport mechanism can incorporate any conventional transporting device, such as a system of transport rollers, a conveyor belt system, a system of gas jets, an electromagnetic suspension system, or the like, as well as combinations thereof.

The technique of the invention can form an article, such as the representatively shown absorbent web 26, and the article can include a distinctive distribution of a selected binder or agent material within a matrix of fibers. Desirably, the absorbent web or other article can be distinctively configured with a plurality of strata, which can be distinctively arranged along a z-directional, thickness dimension or direction 123 (e.g. FIG. 5). In particular arrangements, the selected fibrous material can also provide an operative fibrous matrix for holding and containing a superabsorbent material, The process for forming the absorbent web 26 can include an airlaying of a first fibrous stratum 28 which has a first quantity of absorbent fibers; an airlaying of a second fibrous stratum 34 which has a second quantity of absorbent fibers; and an airlaying of a third, intermediate fibrous stratum 40 which has a third quantity of absorbent fibers. The intermediate fibrous stratum has a location that is interposed between the first fibrous stratum and the second fibrous stratum. A liquid, wet-strength agent is distributed onto the fibers of the intermediate fibrous stratum 40 during the airlaying of the intermediate fibrous stratum to thereby render the intermediate fibrous stratum substantially non-dispersible.

Generally stated, the apparatus 20 for forming the absorbent web 26 includes a conventional fiber source, such as provided by the representatively shown fiberizer 74. The fiber source can supply fibers for airlaying onto a forming surface 22 to provide a first fibrous stratum 28 having a first quantity of absorbent fibers, a second fibrous stratum 34 having a second quantity of absorbent fibers, and an intermediate fibrous stratum 40 having a third quantity of absorbent fibers. The intermediate fibrous stratum has a location that is interposed between the first fibrous stratum and the second fibrous stratum; and desirably, is integrally formed with the first fibrous stratum and the second fibrous stratum. An applicator, such as provided by the representatively shown nozzle 60 can distribute a liquid, wet-strength agent onto the fibers of the intermediate fibrous stratum 40 during the airlaying of the intermediate fibrous stratum.

The process and apparatus are configured to operatively form or join the intermediate fibrous stratum 40 with at least the first fibrous stratum 28. Desired aspects of the invention can integrally form or join the intermediate fibrous stratum 40 with both of the first and second fibrous strata 28 and 34, respectively, and in further aspects, the invention can configure the first and second fibrous strata 28 and 34 to be substantially dispersible in an aqueous liquid. In a particular aspect, the composite strata of the web 26 can be operatively compressed prior to a curing of the wet-strength agent.

In desired configurations, the airlaying of the first fibrous stratum 28 provides a first stratum which has a first quantity of absorbent fibers 94, and the airlaying of the second fibrous stratum 34 provides a second stratum which has a second quantity of absorbent fibers. Additionally, the third, intermediate fibrous stratum 40 can be airlaid to include a third quantity of absorbent fibers. The intermediate stratum is integrally formed with the first fibrous stratum 28, and has an appointed location that is interposed between the first fibrous stratum and the second fibrous stratum. In desired arrangements, the intermediate stratum can be integrally formed with the first and second fibrous strata 28 and 34. As representatively shown in FIG. 1, for example, the illustrated configuration can incorporate a single forming chamber 24 to help reduce equipment costs, and can locate inside the forming chamber a nozzle system 48 for applying the wet-strength agent. Accordingly, the liquid, wet-strength agent can be selected and arranged to provide the intermediate fibrous stratum 40 with the desired configuration that is substantially non-dispersible in an aqueous liquid.

Additionally, the first and second fibrous strata can be configured to remain substantially dispersible in an aqueous liquid. In desired aspects, the process and apparatus can be configured to substantially avoid distributing the wet-strength agent into the first fibrous stratum 28, and in further aspects, the process and apparatus can be configured to substantially avoid distributing the wet-strength agent into the second fibrous stratum 34.

With reference to FIG. 2, an alternative arrangement of the invention can include a selected plurality of forming chambers, such as provided by chambers 24 and 24a. Additionally, the nozzle system 48 for applying the wet-strength agent can be located outside the forming chambers and between an adjacent pair of the forming chambers. In particular arrangements, fibers in the first forming chamber 24 can be mixed or otherwise combined with superabsorbent particles which are delivered through a first superabsorbent nozzle 78. The resulting mixture of fibers and superabsorbent particles are deposited onto the foraminous forming surface 22, and a vacuum source 66 is located below the forming surface to generate the operative forming air flow through the forming surface. After the partially formed composite web exits the first forming chamber 24, the web passes under the agent nozzle system 48. The wet-strength agent is directed towards the exposed, top surface of the composite, and is operatively applied to the intermediate fibrous stratum 40. The partially formed composite web and applied agent can then be directed to enter the second chamber 24a where the second fibrous stratum 34 can be airlaid or airformed onto the intermediate fibrous stratum. Alternatively, the forming system can have one or more forming chambers that include rotatable, vacuum-forming drums. Optionally, the multiple forming chambers can include combinations of flat-wire forming surfaces and rotatable drum forming surfaces.

In still other configurations, the forming chamber system representatively shown in FIG. 1 may be combined with one or more of the forming chamber systems illustrated in FIG. 2. Accordingly, the airlaying of the first fibrous stratum 34 and the airlaying of the intermediate fibrous stratum 40 may be conducted within the first forming chamber 24 and the airlaying of at least a major portion, and desirably substantially all, of the second fibrous stratum may be conducted within the second forming chamber 24a. Additionally, the applicator nozzle 60 for the wet-strength resin can be located in the first forming chamber 24 to distribute the wet-strength resin during the airlaying of the intermediate fibrous stratum 40.

It has been found that it is advantageous to incorporate a binding compound or other wet-strength agent that has a high capability of penetrating into and through a selected thickness dimension of the absorbent web 26. In desired aspects, the wet-strength agent has a high capability of penetrating into and through a selected thickness dimension of the intermediate fibrous stratum 40. Accordingly, the process and apparatus of the invention can desirably employ a wet-strength agent that has a low viscosity.

The various configurations of the invention incorporate a suitable fiber source, such as a supply system that includes a conventional fiberizer 74, and the fiber source can operatively deliver fibers for the desired airlaying onto the forming surface 22. Typically, the desired fibrous material can be delivered through a suitable conduit into the fiberizer in a conventional raw material form, such as a sheet form, a bale form or the like. Accordingly, the system can deliver the first quantity of airlaid absorbent fibers 94 for the first fibrous stratum 28, the second quantity of airlaid absorbent fibers for the second fibrous stratum 34, and the third quantity of airlaid absorbent fibers for the intermediate fibrous stratum 40. The airlaying of the intermediate fibrous stratum 40 can superpose the intermediate fibrous stratum directly onto the immediately adjacent first fibrous stratum 28, and the airlaying of the second fibrous stratum 34 can thereafter superpose the second fibrous stratum directly onto the immediately adjacent, intermediate fibrous stratum 40.

The technique of the invention can also include an agent applicator nozzle 60 (e.g. FIG. 1) which operatively distributes the liquid, wet-strength agent onto the fibers of the intermediate fibrous stratum 40 for the purpose of eventually configuring the intermediate fibrous stratum to be substantially non-dispersible in an aqueous liquid. In particular configurations, the nozzle can operatively distribute the wet-strength agent during and substantially concurrently with the airlaying of the intermediate fibrous stratum. In other arrangements, the nozzle can distribute the wet-strength agent during an operation that is substantially isolated and separated from the airlaying of the intermediate fibrous stratum. Further aspects of the invention can incorporate a nozzle assembly which includes the agent nozzle 60 and an associated housing 50 (e.g. FIG. 4). The nozzle housing 50 can be distinctively configured to provide a selected stream of a purging airflow, which can help prevent an excessive clogging or other fouling of the agent nozzle.

Other aspects of the invention can include a moving of a foraminous forming surface 22 through the forming chamber 24, and an airlaying of the first fibrous stratum 28 on the forming surface 22. Desired arrangements can incorporate a transporter, such as provided by the representatively shown system of rollers 86, which operatively move the forming surface 22 in and through the forming chamber 24. Additional aspects of the invention can include a scarfing or other leveling of the absorbent web 26 with a scarfing roll 70, and the scarfing can be configured to remove a selected portion of the second fibrous stratum 34. In desired configurations, the scarfing roll 70 and scarfing operation can be configured to substantially avoid removing fibrous material which includes a significant amount of the wet-strength agent. In particular arrangements, the scarfing roll 70 and scarfing operation can be configured to substantially avoid removing fibrous material the intermediate fibrous stratum 40. Further aspects can include a system for densifying of the absorbent web, such as a system provided by the illustrated compression rollers 126. Additional aspects can include a discrete system for curing the wet-strength agent.

In the shown configurations, the technique of the invention can form a substantially continuous, fibrous web 26 which extends longitudinally along the appointed machine-direction 120. Optionally, the technique may be configured to continually produce a segmented web, or a plurality of individually discrete and separate webs that are discontinuously or intermittently arranged along the machine-direction. The web segments or individual webs may, for example, be positioned side-by-side along the cross-direction, positioned in series along the machine-direction, or positioned in combinations of such side-by-side and serial arrangements. In optional configurations, one or more selected strata may be discontinuously formed. For example, the intermediate fibrous stratum 40 may be intermittently formed along the machine-direction 120, and/or may be intermittently formed along the cross-direction 122. Similarly, the second fibrous stratum 34 may be intermittently formed along the machine-direction and/or cross-direction. It should be readily appreciated that the various arrangements of the fibrous web are desirably composed of one or more materials that make the web absorbent to liquids, such as water, menses and/or urine.

Conventional air-forming systems have employed forming chambers to produce fibrous absorbent webs that contain binder materials and/or particles of superabsorbent materials. For example, composite "coform" webs have constructed to include combinations of cellulose fibers, superabsorbent particles and binder fibers. The binder fibers have been composed of synthetic polyolefins, such as polypropylene, or other synthetic polymers.

Multiple forming chambers have been employed to form layered, composite webs, with each web layer containing a selected amount or type of airlaid fiber material and superabsorbent material. Other layered webs have been produced by stacking individual layers after the layers have been previously formed. Such conventional techniques have, however, required excessive amounts of expensive equipment and excessive amounts of factory space. In addition, such conventional techniques have not adequately controlled the distributions and placements of selected materials, such as binder materials, through the thickness dimension of the overall, formed web, and have not sufficiently regulated the amounts and concentrations of the selected material at the desired placements. Where preformed layers are stacked in a conventional manner to produce the final composite web, the interfaces between the stacked layers can excessively inhibit or otherwise degrade the desired transfer of liquid between the immediately adjacent layers.

In its various configurations and aspects, alone and in combination, the technique of the present invention can advantageously provide an improved method and apparatus for forming an article having a plurality of strata, with each stratum composed of fiber material, wet-strength agent and superabsorbent material and in a selected combination. The technique of the invention can provide an efficient and cost effective technique for producing a desired distribution of wet-strength agent in at least one stratum which is selectively positioned along the thickness dimension of the absorbent web 26. Additionally, the process and apparatus can be selectively adjusted to generate desired distributions and/or concentrations of the wet-strength agent within its corresponding, appointed stratum. The invention can also efficiently locate the wet-strength within its corresponding, appointed strata at desired positions along the thickness dimension, machine-direction and/or cross-direction of the formed web 26. Thus, the technique of the invention can advantageously produce a stratified and unitary, composite web having a more effective transport and distribution of absorbed liquid along and through selected strata. For example, the technique can be configured to produce a desired blending or other graduated transition between the component materials of immediately adjacent strata. As a result, the technique of the invention can help produce a composite web having an improved flow and transfer of liquid through the composite web thickness and between immediately adjacent strata. The invention can also be configured to be less susceptible to clogging, and to form multiple strata within a single forming chamber. As a result, the technique of the invention can be conducted with smaller amounts of expensive equipment, can be operated with lower costs, and can be more reliably and more efficiently conducted in a small operating space.

As illustrated in FIGS. 1 and 2, a representative method and apparatus for forming the desired article, such as the shown absorbent web structure 26, includes a transporter which moves a foraminous forming surface 22 through an operative forming chamber 24 along an selected forming path length 118. The transporter can, for example, include a system of guide rollers and drive rollers 86, and the forming surface 22 can be provided by a recirculating, endless belt, forming screen. An operative portion of the forming surface is surrounded and enclosed by the forming chamber 24. Conventional airlaying or air forming systems which incorporate an endless forming belt are well known in the art. For example, conventional belt forming systems are available from the Paper Converting Machine Corp., a business having offices located in Green Bay, Wis.

Alternative arrangements of the invention can employ a rotatable, vacuum forming drum which is operatively enclosed by the forming chamber 24. The forming drum can have a circumferential, outer periphery which provides the foraminous forming surface 22, and the moving of the forming surface can be provided by the rotation of the forming drum. The selected forming drum can be constructed and configured with a conventional "vacuum" system which generates a primary, air stream or airflow which moves from the interior of the forming chamber 24, through the forming surface 22 and into the interior of the forming drum 64. Examples of suitable forming drum systems for producing airlaid fibrous webs are well known. For example, see U.S. Pat. No. 4,666,647 entitled APPARATUS AND METHOD FOR FORMING A LAID FIBROUS WEB by K. Enloe et al. which issued May 19, 1987; U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent (not in contradiction) herewith.

A conventional source of the selected fibrous material, such as a supply reservoir or a conventional fiberizer 74, can be configured to provide an operative supply of fiber material into the forming chamber 24. As representatively shown, the fiberizer 74 can be operatively positioned above the forming chamber and can include a conventional, rotary hammermill. In alternative arrangements, the fiberizer may be located to the side of the forming chamber, or may be positioned at a remote location that is spaced away from the forming chamber.

The fiber material may include natural fibers, synthetic fibers, and combinations thereof. Examples of natural fibers can include wood pulp fibers, cotton fibers, wool fibers, silk fibers and the like, as well as combinations thereof. Synthetic fibers can include rayon fibers, polyolefin fibers, polyester fibers and the like, as well as combinations thereof. Typically, the fiber material includes woodpulp cellulose fibers.

In desired aspects, at least one of the first, second and/or third quantities of absorbent fibers can include hydrophilic fibers. In desired configurations, each of the first, second and third quantities of absorbent fibers can include hydrophilic fibers. In further aspects, at least one of the first, second and/or third quantities of absorbent fibers can include cellulosic fibers. In desired arrangements, the quantities of absorbent fibers in each of the first, second and third fibrous strata can include cellulosic fibers.

With reference to FIG. 1, the forming chamber 24 typically includes a front entrance wall 102, a rear exit wall 104, an appropriate pair of opposed side walls 103 (one of which, for the purpose of clarity, is not shown), and a top cover wall 108, which are assembled together and configured in a conventional manner to suitably enclose and surround an operative internal, forming volume of the forming chamber 24. As the forming belt 64 translates through the forming chamber, the fiber material is entrained by the air stream of the primary airflow that is being drawn through the forming surface 22, and the fibers thereby become deposited onto the forming surface. The fiber material is gradually accumulated onto the outer peripheral, forming surface 22 as the rotating forming drum moves the forming surface through the forming chamber. During the movement of the forming surface, the rate of the fiber accumulation and amount of the fibrous web formation will vary, depending upon the process position along the machine-directional length of the forming chamber. The greater rates of fiber accumulation and the greater amounts of web formation will typically occur towards the beginning, entrance-wall end of the forming chamber. Relatively smaller rates of fiber accumulation and relatively smaller amounts of web formation will typically occur towards the ending, exit-wall end of the forming chamber. After leaving the airlaying operation of the forming chamber, the formed web 26 can be subjected to further processing and assembly operations. For example, the web may be debulked and densified, and the web may be assembled with other desired components to form a final, finished article.

The forming surface 22 is typically a foraminous, air permeable component, such as provided by a wire forming cloth, a screen, a perforated plate or the like, as well as combinations thereof. Additionally, the air permeable component may be composed of any sufficiently durable material, such as metal, plastic, ceramic or the like, as well as combinations thereof. For example, the forming surface may be composed of brass or stainless steel. The forming surface may also include a porous tissue, a woven fabric, a nonwoven fabric or the like, as well as combinations thereof.

With reference to FIGS. 1 and 2, the forming chamber 24 can delimit a forming path length 118 which corresponds to the length of the forming surface 22 which, at any particular point in time, is positioned within the forming chamber and between the forming chamber entrance 98 and the forming chamber exit 100. Accordingly, the forming path length 118 begins at a first-occurring forming chamber entrance (e.g. entrance 98) and extends along the forming surface 22 to end at a last-occurring forming chamber exit (e.g. exit 100 in FIG. 1; exit 100a in FIG. 2). As representatively shown, constantly changing portions or sections of the translating forming belt 64 follow one another in sequence to become positioned along the forming path length during the movement of the forming belt. In the representatively shown arrangement that employs the endless-belt forming surface, the forming path length 118 lies along a substantially straight line. Where the forming surface 22 is provided by a rotatable forming drum, it should be readily appreciated that the forming path length is arcuate and extends along a circular or otherwise curved line that generally corresponds to the peripheral, circumferential dimension of the forming drum.

In a particular aspect of the invention, the moving of the forming surface 22 can operatively translate the forming surface at a surface speed which is at least a minimum of about 100 m/min. The surface speed can alternatively be at least about 200 m/min, and optionally, can be at least about 300 m/min to provide improved performance. In other aspects, the surface speed can be up to a maximum of about 1000 m/min, or more. The surface speed can alternatively be not more than about 800 m/min, and optionally, can be not more than about 700 m/min to provide improved effectiveness.

The absorbent web 26 can be airlaid at an average rate which is at least a minimum of about $1*10^3$ g/m$^2$ per minute. The airlaying rate can alternatively be at least about $5*10^3$ g/m$^2$ per minute, and optionally, can be at least about $1*10^4$ g/m$^2$ per minute to provide improved performance. In other aspects, the airlaying rate can be not more than a maximum of about $2*10^5$ g/m$^2$ per minute. The airlaying rate can alternatively be not more than about $1*10^5$ g/m$^2$ per minute, and optionally, can be not more than about $5*10^4$ g/m$^2$ per minute to provide improved effectiveness.

If the rate of airlaying is too low, the formation of the absorbent web may not be sufficiently uniform, and the basis weight of the formed web may be too low. As a result, the web may not have enough strength to accommodate further processing operations. If the rate of airlaying is too large, the basis weight of the formed web may be too high. The high basis weight of the formed web can excessively inhibit or disrupt the desired airflows through the forming chamber 24 and forming surface 22, and can require the use of more expensive equipment.

With reference to FIG. 1, the first fibrous stratum 26 is formed during the movement of the forming surface 22 along a first section of the forming path length that is positioned between the forming chamber entrance 98 and a point prior to the location of the agent nozzle 60. Upon its formation, the first fibrous stratum is provided with a first stratum thickness 30 along the z-direction, and a first stratum width 32 along the lateral cross-direction (e.g. FIG. 5 and 5A). The intermediate fibrous stratum 40 is formed during the movement of the forming surface 22 along a subsequent section of the forming path length that is positioned generally proximate the location of the agent nozzle. The intermediate fibrous stratum is provided with an intermediate stratum thickness 42 along the z-direction, and an intermediate stratum width 44 along the lateral cross-direction. The second fibrous stratum is formed along a next section of the forming path length that is positioned after the distribution of the wet-strength agent and before the forming chamber exit 100. The second fibrous stratum is provided with a second stratum thickness 36 along the z-direction, and a second stratum width 38 along the lateral cross-direction. Accordingly, the distributing of the wet-strength agent onto fibers of the third fibrous stratum 40 can occur during the airlaying of the intermediate, third fibrous stratum. The process and apparatus can also restrict, or optionally, substantially isolate the distribution of the wet-strength agent to the intermediate fibrous stratum. Additionally, the process and apparatus can configure the first and second fibrous strata to be substantially free of the wet-strength agent, and can configure the first and second fibrous strata remain soft and substantially dispersible in an aqueous liquid.

With reference to the alternative arrangement representatively shown in FIG. 2, the first fibrous stratum 26 is formed during the movement of the forming surface 22 along a first section of the forming path length that is positioned within the first forming chamber 24. Additionally, the fibrous material appointed for the intermediate fibrous stratum 40 is airlaid directly onto the first fibrous stratum within the first forming chamber. After the partially completed web exits the first forming chamber, the agent nozzle device operatively distributes the liquid wet-strength agent onto the portion of fibrous material that has been appointed for the intermediate fibrous stratum 40. The second fibrous stratum is formed along a next section of the forming path length that is positioned within the second forming chamber 24a. Accordingly, the distribution of the wet-strength agent can operatively be restricted to, or optionally, substantially isolated in the intermediate fibrous stratum. Additionally, the technique of the invention can configure the first and second fibrous strata to be substantially free of the wet-strength agent, and can configure the first and second fibrous strata to remain soft and substantially dispersible in an aqueous liquid.

In the various configurations of the invention, the distributing of the liquid wet-strength agent 46 can be accomplished by employing any conventional technique, such as sprinkling, spraying or the like, as well as combinations thereof. As representatively shown, the distributing of the liquid, wet-strength agent can employ a nozzle mechanism 60. The nozzle may, for example, be a component of any suitable spraying system, such as hydraulic spray systems, air atomizing spray systems, ultra-sonic spray systems and the like; or printing techniques, such as ink jet printing and the like; as well as combinations thereof.

In desired arrangements, the technique of the invention can employ a flat-pattern spray nozzle in which the longest dimension of the spray pattern is aligned generally along the cross-direction 122 of the method and apparatus. A suitable flat-pattern spray nozzle is a UNIJET 5002 nozzle which is available from the Spraying Systems Company, a business having offices located in Wheaton Illinois. In particular arrangements, the spray nozzle can have a spray orifice diameter which is within the range of about 0.25–2.5 mm.

Figure 4:
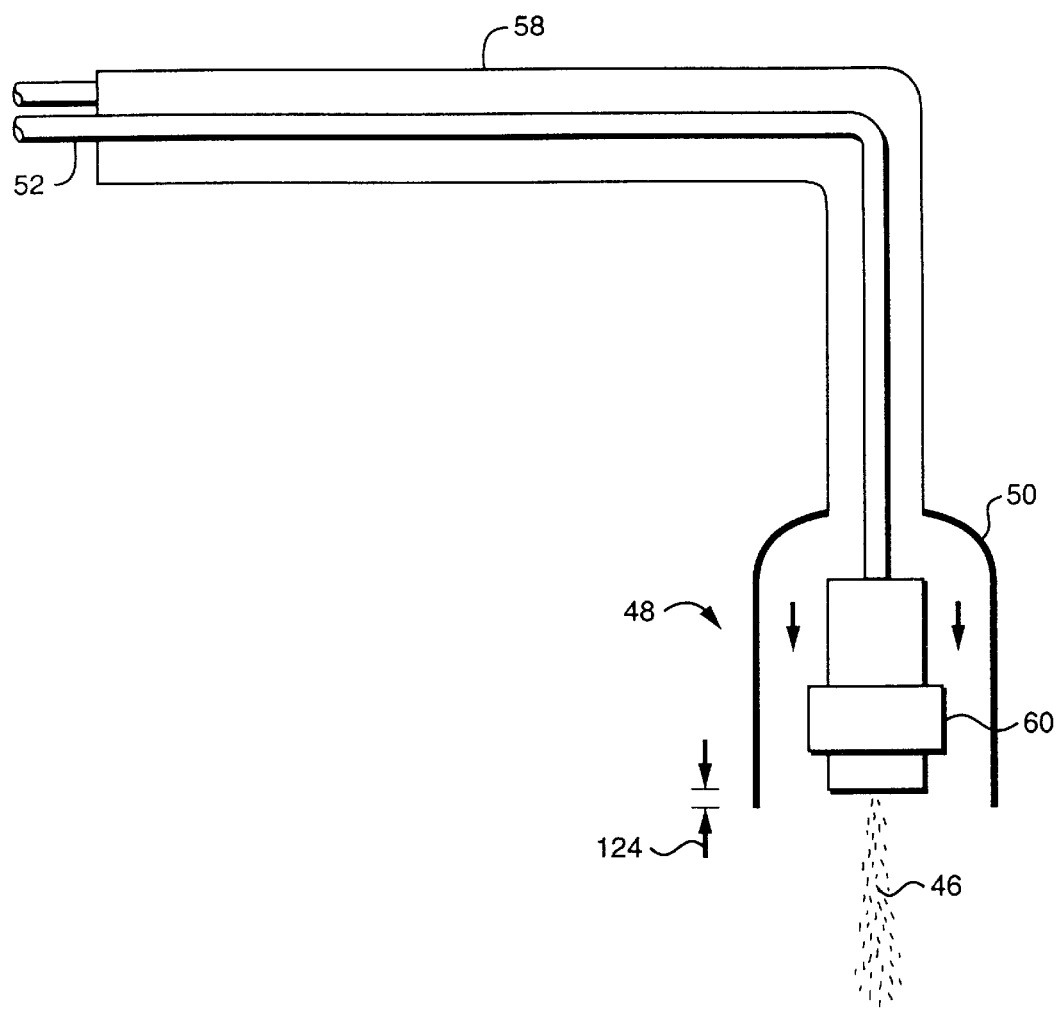
FIG. 4 representatively shows a nozzle system that can be employed by the present invention.

Other particular aspects of the invention can include a distinctive spray nozzle assembly 48 which includes the nozzle 60, an outer housing 50 and an associated gas conduit 58, as representatively shown in FIG. 4. The outer housing 50 is arranged approximately co-axially around the spray nozzle 60, and extends axially in a lengthwise direction beyond a terminal, outlet end of the spray nozzle 60. The gas conduit 58 is operatively connected to deliver a stream of purging gas into and through the outer housing 50.

The nozzle assembly 48 may be mounted to a suitable support, such as the front entrance wall 102 (e.g. FIG. 1), and the nozzle assembly can be configured to direct and regulate a flow of the liquid wet-strength agent into the forming chamber 24. The agent nozzle 60 can be located, oriented and aligned to direct the liquid wet-strength agent into the accumulating web along a corresponding, appointed section of the forming path length. The selected position of the agent nozzle above the forming surface 22 and the location of the agent nozzle along the forming path length can be selectively adjusted to regulate the placement of the wet-strength agent along the thickness dimension of the overall web 26.

The agent spray nozzle 60 can be placed at a selected height distance 116 above the forming surface 22, and the height distance is measured along a straight reference line that intersects the center of the outlet orifice of the nozzle 60 and extends perpendicular to the forming surface at the local position of the spray nozzle 60. In desired configurations, the height distance 116 can be at least a minimum of about 10 mm. The height distance can alternatively be at least about 40 mm, and optionally, can be at least about 80 mm to provide improved performance. In other aspects, the height distance can be not more than a maximum of about 250 mm. The height distance can alternatively be not more than about 200 mm, and optionally, can be not more than about 150 mm to provide improved effectiveness.

If the height distance is too small, the process and apparatus can excessively interfere with the formation of the absorbent web, and can increase the likelihood of plugging in the agent nozzle. If the height distance is too large, it can be excessively difficult to control maintain the desired distribution stream of agent from the agent nozzle.

In a desired aspect, the agent nozzle 60 is positioned at a selected location along the forming path length 118 within the forming chamber 24. Taking the entrance 98 of the forming chamber 24 as being the zero point of the forming path length 118, the agent nozzle 60 can have a selected position along the forming path length 118 within the forming chamber 24, as representatively shown in FIG. 1. The agent nozzle 60 can have a path position distance 61 which is at least a minimum of about 5% of the overall forming path length 118. The path position distance can alternatively be at least about 20% of the overall forming path length, and optionally, can be at least about 30% of the overall forming path length to provide improved performance. In other aspects, the path position distance can be not more than a maximum of about 95% of the overall forming path length. The path position distance can alternatively be not more than about 80% of the overall forming path length, and optionally, can be not more than about 70% of the overall forming path length to provide improved effectiveness.

The path position distance 61 of the agent nozzle 60 can advantageously be adjusted to control the placement of the wet-strength agent along the thickness dimension 90 of the absorbent web 26, and can control the location of the intermediate fibrous stratum 40 along the overall thickness of the absorbent web 26. If the path position distance 61 of the agent nozzle 60 is too small, the thickness of the first fibrous stratum 28 can be too small. Additionally, the liquid agent may be positioned too close to the forming-surface side of the absorbent web, and the agent may be readily exposed and excessively contaminate the components of the method and apparatus. If the path position distance 61 of the agent nozzle 60 is too large, the thickness of the second fibrous stratum 34 can be too small. Additionally, the liquid agent may be positioned too close to the fiberizer-side of the absorbent web, and the agent may again be readily exposed and excessively contaminate the components of the method and apparatus.

Various techniques may be employed to observe the location of the intermediate fibrous stratum 40. For example, an inert colorant or other indicator may be substituted for or temporarily added to the liquid wet-strength agent, and the position and distribution of the indicator may be visually or electronically observed in a cross-section taken through the absorbent web 26. The various parameters of the process and apparatus can then be adjusted to move the position of the observed indicator to a desired location. It should be readily appreciated that the indicator should be selected and employed in a manner that generates an accurate replication of the movement and distribution of the original, wet-strength agent into the appointed fibrous web material. For example, the indicator should preserve the viscosity and wettability characteristics of the original, wet-strength agent.

The distributing of the liquid, wet-strength agent 46 onto the fibers of the intermediate fibrous stratum 40 can operatively deposit the wet-strength agent substantially continuously along a lengthwise machine-direction 120 of the process. Optionally, the liquid, wet-strength agent can be distributed onto the fibers of the intermediate fibrous stratum in an intermittent or otherwise discontinuous arrangement along the lengthwise machine-direction. Additionally, the wet-strength agent can be distributed in a selected, regular or irregular pattern.

Figure 5:
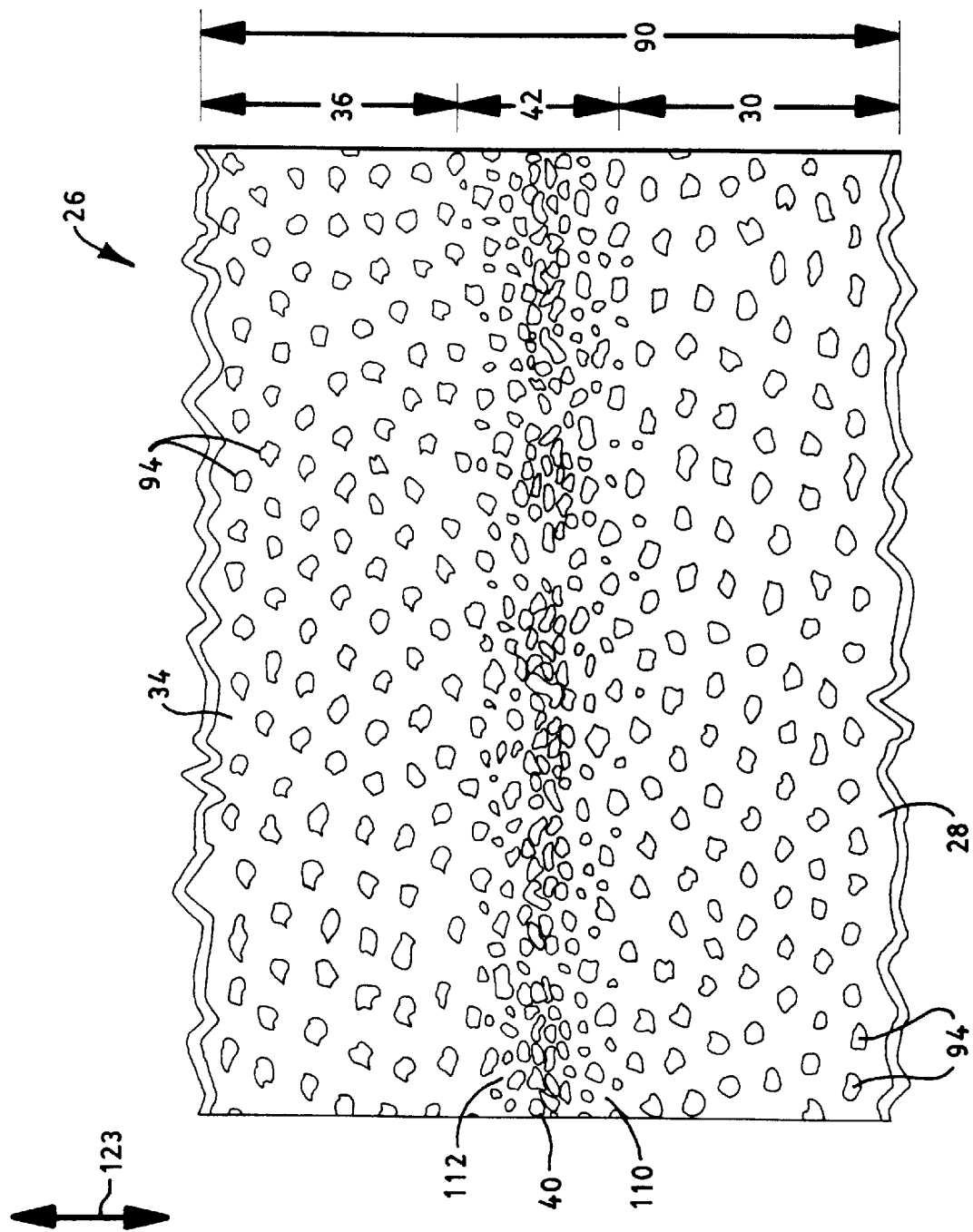
FIG. 5 representatively shows a schematic cross-sectional view of a stratified absorbent web that is constructed with the present invention.
Figure 5A:
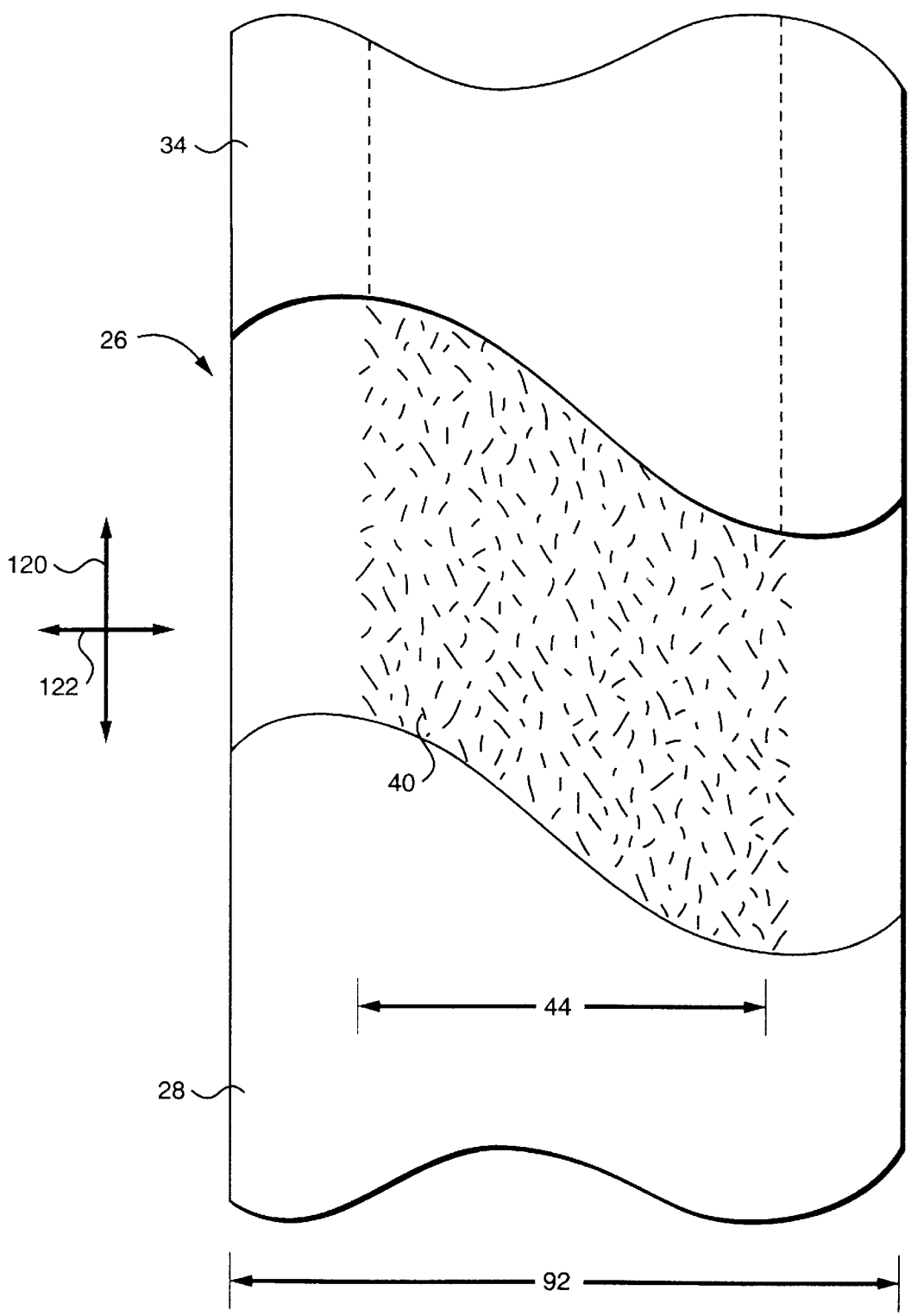
FIG. 5A representatively shows a schematic, partially cut-away, top view of the web illustrated in FIG. 5.

With reference to FIGS. 1A and 5A, the distributing of the liquid, wet-strength agent onto the fibers of the intermediate fibrous stratum 40 can deposit the wet-strength agent along a cross-directional width 44 which is at least a minimum of about 5% of a cross-directional width 27 of the absorbent web 26. The cross-directional width over which the agent is deposited can alternatively be at least about 15%, and optionally, can be at least about 25% of the cross-directional width of the absorbent web to provide improved performance. In other aspects, the cross-directional width over which the agent is deposited can be not more than a maximum of about 100% of the cross-directional width of the absorbent web. The cross-directional width over which the agent is deposited can alternatively be not more than about 90%, and optionally, can be not more than about 80% of the cross-directional width of the absorbent web to provide improved effectiveness. As a result, the applied wet-strength agent can operatively reinforce the intermediate fibrous stratum 40 over a selected width which corresponds to the width 44 of the deposited wet-strength agent.

In more particular arrangements, the distributing of the liquid, wet-strength agent onto the fibers of the intermediate fibrous stratum 40 can deposit the wet-strength agent along a cross-directional width 44 which is at least a minimum of about 5% of a cross-directional width 32 of the first fibrous stratum 28. The cross-directional width over which the agent is deposited can alternatively be at least about 15%, and optionally, can be at least about 25% of the cross-directional width of the first fibrous stratum to provide improved performance. In other aspects, the cross-directional width over which the agent is deposited can be not more than a maximum of about 100% of the cross-directional width of the first fibrous stratum. The cross-directional width over which the agent is deposited can alternatively be not more than about 90%, and optionally, can be not more than about 80% of the cross-directional width of the first fibrous stratum to provide improved effectiveness.

Similarly, the distributing of the liquid, wet-strength agent 46 onto the fibers of the intermediate fibrous stratum 40 can deposit the wet-strength agent along a cross-directional width 44 which is at least a minimum of about 5% of a cross-directional width 38 of the second fibrous stratum 34. The cross-directional width over which the agent is deposited can alternatively be at least about 15%, and optionally, can be at least about 25% of the cross-directional width of the second fibrous stratum to provide improved performance. In other aspects, the cross-directional width over which the agent is deposited can be not more than a maximum of about 100% of the cross-directional width of the second fibrous stratum. The cross-directional width over which the agent is deposited can alternatively be not more than about 90%, and optionally, can be not more than about 80% of the cross-directional width of the second fibrous stratum to provide improved performance.

If the width 44 of the agent distribution is too small, the intermediate fibrous stratum 40 will not provide adequate levels of wet- strength and integrity in the absorbent web. If the width 44 of the agent distribution is too large, the intermediate stratum 40 may be excessively exposed to other components of the process and apparatus. For example, an exposed intermediate stratum can excessively contaminate the surface of the debulker, compression rollers 126.

With reference to FIG. 1A, the agent nozzle 60 can have a selected location along the cross-directional width of the forming surface 22. With reference to a centerline which is substantially centered along the cross-direction 122 of the forming surface 22, and extends longitudinally along the machine-direction 120, the agent nozzle 60 can have a lateral offset position which is within the range of about 0–10% of a cross-directional width of the forming surface 22. The lateral, cross-directional offset of the agent nozzle 60 can be with respect to either side of the centerline of the forming surface 22.

It should be readily appreciated that various suitable techniques may be employed to place the agent in the desired liquid form. For example, the liquid, wet-strength agent can be liquefied or otherwise placed into its liquid condition by a melting of the agent, a dissolving of the agent in an operative liquid to provide a solution, a suspending or emulsifying of the agent in an operative liquid, or the like, as well as combinations thereof.

The liquid, wet-strength agent can have a viscosity which is at least a minimum of about 1 centipoise (cP). In other aspects, the viscosity can be not more than a maximum of about 500 cP. The viscosity can alternatively be not more than about 250 cP, and optionally, can be not more than about 50 cP to provide improved effectiveness.

If the viscosity is too low, the concentration of the wet-strength agent may be too low to provide the desired levels of effectiveness and wet-strength. If the viscosity is too high, the equipment needed to apply the wet-strength agent may be excessively complicated and expensive. For example, sophisticated equipment may be required to generate the high pressures needed for spraying high-viscosity liquids. In addition, the high-viscosity agent may not be sufficiently able to penetrate through a desired thickness dimension of the absorbent web 26, particularly through a desired thickness dimension of the intermediate fibrous stratum 40. As a result, the high viscosity agent may not provide the desired, diffuse interfaces at the boundaries of the intermediate fibrous stratum, and may not provide the desired density gradients along the thickness dimension of the intermediate fibrous stratum.

In particular aspects, the liquid, wet-strength agent can provide an amount of agent solids that is at least a minimum of about 0.05 wt % of the overall, total absorbent web 26. The amount of agent solids can alternatively be at least about 0.1 wt %, and optionally, can be at least about 0.2 wt % of the overall, total absorbent web to provide improved performance. In other aspects, the amount of agent solids can be not more than a maximum of about 5 wt % of the overall, total absorbent web. The amount of agent solids can alternatively be not more than about 2 wt %, and optionally, can be not more than about 1 wt % of the overall, total absorbent web to provide improved effectiveness. In the various configurations, the amount of agent solids can represent a dry add-on amount of the agent solids.

If the add-on amount of agent solids is too small, the intermediate fibrous stratum 40 will not provide adequate levels of wet- strength and integrity in the absorbent web. If the amount of agent solids is too large, the absorbent web can be excessively stiff.

In particular aspects, the liquid, wet-strength agent 46 can be distributed into the intermediate fibrous stratum at a rate which is at least a minimum of about 40 g/min. The distribution rate can alternatively be at least about 400 g/min, and optionally, can be at least about 2000 g/min to provide improved performance. In other aspects, the distribution rate can be not more than a maximum of about 40,000 g/min. The distribution rate can alternatively be not more than about 10,000 g/min, and optionally, can be not more than about 6,000 g/min to provide improved effectiveness.

If the distribution rate of the liquid, wet-strength agent is too low, the uniformity of the agent distribution may be inadequate, and the intermediate fibrous stratum 40 may not provide adequate levels of wet-strength and integrity in the absorbent web. If the distribution rate of the liquid, wet-strength agent is too high, it may be excessively difficult to dry or otherwise cure the wet-strength agent. Where the liquid agent includes a solvent, for example, the removal of large amounts of the solvent can be excessively expensive and complicated.

In desired configurations, the liquid, wet-strength agent 46 is capable of wetting the fibers in the intermediate fibrous stratum 40. In particular aspects, the liquid, wet-strength agent includes an aqueous liquid. In other aspects, the wet-strength agent can be a water-based liquid. Additionally, the wet-strength agent can be substantially hydrophilic, particularly when the wet-strength agent is in its cured state. Such properties can, for example, help to enhance the movement and distribution of the liquid agent along an around individual fibers, and can enhance the wet-strength of the intermediate fibrous stratum. The properties can also help to improve the transport of absorbed liquids along and through the intermediate stratum.

A suitable wet-strength agent can be of a polymeric or non-polymeric binder material that is capable of forming hydrogen bonds, ionic bonds or covalent bonds with the selected fiber(s) employed with the present invention. Accordingly, the appropriate liquid binder can be fiber-specific, and different fibers may require a different liquid binder to provide the desired performance. In desired configurations, the binder material can be a water-based solution. For cellulose fibers, suitable binders are well known to those skilled in the art.

Examples of suitable polymeric binders can include polypropylene glycol (PPG); polyethylene glycol (PEG); polyacrylic acid (PM); poly(caprolactone) diol; polyamide; cationic acrylamide copolymers; polyamine; polyamide-polyamine-epichlorohydrin (KYMENE); cationic amine-epichlorohydrin wet strength agents; polyethylene imine agents; polyamide-epichlorohydrin agents with cellulose ethers or cationic starches for improving paper wet strength; polyacrylamides-glyoxal (e.g. PAREZ); urea-formaldehyde agents (UF); cationic modified ureaformalin agents; melamine-formaldehyde agents (MF); cationic modified melamine-formalin agents; polyethyleneimine (PEI); dialdehyde starch (DAS); proteinaceous adhesives treated with formaldehyde; cellulose xanthate (viscose); synthetic latexes; vegetable gums such as guar and bean gum; neutral (or alkaline-curing) thermosetting wet-strength agents; water-soluble polymers containing carboxyl groups or carboxylate ions as their alkali metal or ammonium salts; substantially non-thermosetting tertiary-amino polyamide-epichlorohydrin agents.

Some commercial liquid binders are KYMENE 557LX, a polyamidoamine modified with epichlorohydrin (Hercules); CREPEPLUS 75, 97, a polyamidoamine modified with low epichlorohydrin content (Betz Paper Chemicals); CREPETROL 190, a polyamidoamine modified with low epichlorohydrin content (Hercules); PEI, polyethylenimine, molecular weight 50,000–60,000, 50% (wt) in an aqueous liquid (Aldrich Chemical Co.); PEI-E a polyethylenimine modified with epichlorohydrin, base polymer mol. wt. 20,000, 17% (wt) in an aqueous liquid (Aldrich Chemical Co.); POLYMIN PR971L, a high charge density, high molecular weight polyethylenimine (BASF); POLYMIN SNA, a modified high molecular weight polyethylenimine (BASF); and AGEFLOC WT-20VHV, a poly (dimethyldiallylammonium chloride) (CPS Chemical).

Examples of non-polymeric binders can include glycerin; ascorbic acid; urea; glycine; pentaerythritol; a monosaccharide or a disaccharide; citric acid; glyoxal; tartaric acid; dipropylene glycol; and urea derivatives such as DMDHEU (dimethyldihydroxyethylurea).

Suitable saccharides can include glucose, sucrose, lactose, ribose, fructose, mannose, arabinose, and erythrose.

In desired configuration, the wet-strength agent can include a poly(aminoamide)-epichlorohydrin material, such as KYMENE agent, which is available from Hercules Inc., a business having offices located in Wilmington, Del. In other desired configurations, the wet-strength agent can include a glyoxalated polyacrylamide material, such as PAREZ agent, which is available from Cytec Inductries, a business having offices located in Paterson, N.J.

In particular configurations of the invention, the wet-strength agent can include a poly(aminoamide)-epocholorohydrin material. In other configurations, the wet-strength agent can include a glyoxylated polyacrylamide material.

With reference to FIGS. 5 and 5A, the distinctive configurations of the apparatus and method of the invention can form a diffuse interface 110 between the intermediate fibrous stratum 40 and the first fibrous stratum 28. In other aspects, the technique of the invention can include a forming of a diffuse interface 112 between the intermediate fibrous stratum 40 and the second fibrous stratum 34. As representatively shown, the diffuse interfaces are substantially non-distinct, irregular and substantially non-planar. In desired arrangements, each diffuse interface can represent a substantially continuous, or a substantially continual formation of the immediately adjacent strata.

The various properties of absorbent structures that include components composed of the absorbent web 26 are described in copending U.S. patent application Ser. No. 09/631,494 entitled HIGH-STRENGTH, STABILIZED ABSORBENT ARTICLE by Y. Li et al. which was contemporaneously filed Aug. 31, 2000, the entire disclosure of which is incorporated herein by reference in a manner that is consistent (not contradictory) herewith.

The apparatus and process of the invention can further include a distributing of a selected quantity of the superabsorbent material in the absorbent web 26. With reference to FIG. 1, the superabsorbent material is delivered from a suitable superabsorbent reservoir or supply source 76, and is transported to a superabsorbent nozzle 78 through an appropriate conduit 80. The superabsorbent nozzle 78 is located at a selected position within the forming chamber 24.

As representatively shown, the superabsorbent nozzle 78 can be mounted to a suitable support, such as the front wall 102, and can be configured to direct and regulate a flow of the appointed quantity or quantities of superabsorbent material into the forming chamber 24. The superabsorbent nozzle is desirably oriented and aligned to direct the quantity of superabsorbent material onto an appointed section of the forming path length 118. The directing of the superabsorbent material by the superabsorbent nozzle 78 can operatively combine the quantity or quantities of superabsorbent material with the fibrous material being deposited onto the forming surface 22. As a result, the superabsorbent material can be operatively mixed or otherwise combined with the fibrous material in at least one stratum, and optionally a plurality of appointed strata of the absorbent web 26.

Examples of techniques and nozzle arrangements which can be employed to inject a directed stream of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith.

The superabsorbent nozzle 78 can be configured to provide a substantially continuous delivery or an intermittent delivery of their corresponding superabsorbent materials into the forming chamber. Examples of suitable systems for providing an intermittent or pulsed delivery of superabsorbent material are described in U.S. Pat. No. 5,028,224 entitled METHOD AND APPARATUS FOR INTERMITTENTLY DEPOSITING PARTICULATE MATERIAL IN A SUBSTRATE AND ARTICLE MADE THEREWITH by C. Pieper et al. which issued Jul. 2, 1991, the entire disclosure of which is hereby incorporated by reference in a manner that is consistent herewith.

In particular configurations, the superabsorbent nozzle 78 can be constructed and arranged to provide a substantially uniform distribution of superabsorbent material through the thickness dimension 90 of the absorbent web 26. In other aspects, the superabsorbent nozzle 78 can be configured to provide a relatively greater amount of superabsorbent material in the first fibrous stratum 28, as compared to the second fibrous stratum 34. In further aspects, the superabsorbent nozzle 78 can be configured to provide a relatively greater amount of superabsorbent material in the second fibrous stratum 34, as compared to the first fibrous stratum 28. Additional aspects of the technique of the invention can have an arrangement that forms the first fibrous stratum with a configuration which is substantially free of superabsorbent material.

In desired aspects, the superabsorbent nozzle 78 is positioned at a selected location within the forming chamber 24, as representatively shown in FIG. 1. Taking the entrance 98 of the forming chamber 24 as the zero point of the forming path length 118, the superabsorbent nozzle 78 can have a selected path position distance 79 along the forming path length 118. For example, the path position distance 79 of the superabsorbent nozzle can be 0% of the overall forming path length 118. The path position distance can desirably be at least about at least a minimum of about 1% of the overall forming path length to provide improved performance. In other aspects, the path position distance of the superabsorbent nozzle can be up to 100% of the overall forming path length 118. In desired configurations, the path position distance can be not more than a maximum of about 80% of the overall forming path length 118. The path position distance can alternatively be not more than about 50% of the overall forming path length, and optionally, can be not more than about 30% of the overall forming path length to provide improved effectiveness.

If the path position distance 79 of the superabsorbent nozzle 78 is too small or too large, the superabsorbent material can be positioned excessively close to the top or bottom surface of the absorbent web. As a result, excessive amounts of the superabsorbent may undesirably escape from the web.

The path position distance 79 of the superabsorbent nozzle can be advantageously adjusted to regulate the placement of the superabsorbent material along the thickness dimension 90 of the absorbent web 26. In desired arrangements, the technique of the invention can operatively locate and concentrate the superabsorbent material within a intermediate 80% of the overall thickness of the absorbent web.

In desired aspects, the method and apparatus can provide a quantity of superabsorbent material in the absorbent web 26 which is at least a minimum of about 5 wt % of the overall absorbent web. The quantity of superabsorbent material can alternatively be at least about 10 wt %, and optionally, can be at least about 30 wt % of the overall absorbent web to provide improved performance. In other aspects, the quantity of superabsorbent material in the absorbent web can be not more than a maximum of about 90 wt % of the overall absorbent web. The quantity of superabsorbent material can alternatively be not more than about 60 wt %, and optionally, can be not more than about 50 wt % of the overall absorbent web to provide improved effectiveness.

The agent nozzle 60 can be located upstream from the superabsorbent nozzle 78, and positioned relatively closer to the chamber entrance 24. Alternatively, the agent nozzle 60 can be located downstream from the superabsorbent nozzle 78 and positioned relatively farther from the chamber entrance 98. In the representatively shown configuration, the superabsorbent nozzle 78 is located relatively downstream from the agent nozzle 60. As a result, the superabsorbent nozzle 78 can more effectively distribute the superabsorbent material into the second fibrous stratum 34.

In other desired aspects, the agent nozzle 60 can be positioned relatively closer to the forming surface 22, as compared to the superabsorbent nozzle 78. As a result, the agent nozzle 60 can more effectively and efficiently distribute the wet-strength agent in its desired location, and can provide a better defined intermediate stratum 40.

As the formed fibrous web exits from the forming chamber 24 and/or 24a, a scarfing system can be employed to adjust the basis weight of the formed web. In particular arrangements, the scarfing system can include a rotatable scarfing roll 70 which is configured to contact an exposed surface of the formed, absorbent web 26 and to remove material from the web to provide a more uniform basis weight to the final web. The removed material can be directed through an appropriate, scarfing exit conduit 88 for further processing. The removed material may, for example, be recycled back into the forming chamber, may be recycled into the fiberizer, or may be directed and transported to a supplemental processing operation, as desired.

In other aspects, the technique of the invention can include a compacting and densifying of the absorbent web 26 to a composite density which is at least a minimum of about 0.05 g/cm$^3$. The density can alternatively be at least about 0.08 g/cm$^3$, and optionally, can be at least about 0.15 g/cm$^3$ to provide improved performance. In other aspects, the composite density can be not more than a maximum of about 0.5 g/cm$^3$. The density can alternatively be not more than about 0.35 g/cm$^3$, and optionally, can be not more than about 0.25 g/cm$^3$ to provide improved effectiveness.

The densifying operation can be accomplished by employing any conventional technique. For example, the web may be densified by a compaction press, a system of compression rollers, or the like, as well as combinations thereof.

With reference to FIGS. 1 and 2, a web compactor can operatively compress together the first, second and intermediate fibrous strata, and representatively shown, the web can be operatively compacted and densified by passing the web through the nip of a cooperating pair of counter-rotating compression rollers 126. Accordingly, the composite strata of the assembled web 26 can be de-bulked and compressed together. Preferably, the operative compressing is conducted substantially immediately after the airlaying of the second fibrous stratum 34, and prior to any significant amount of desired curing of the wet-strength agent. Such arrangements can help provide the desired configuration of the intermediate fibrous stratum that is substantially non-dispersible in an aqueous liquid, and can help provide the configuration of the intermediate fibrous stratum that is integrally joined with the first and second fibrous strata.

Desired arrangements of the invention can compress the web 26 within a selected compaction delay time, which is measured between (a) the time that the wet-strength agent has effectively finished being deposited into the intermediate fibrous stratum and (b) the time that the compaction of web has effectively started. In particular aspects, the compaction delay time can be at least a minimum of about 0.001 sec. The compaction delay time can alternatively be at least about 0.05 sec, and optionally, can be at least about 0.1 sec to provide improved performance. In other aspects, the compaction delay time can be not more than a maximum of about 5 sec. The compaction delay time can alternatively be not more than about 2 sec, and optionally, can be not more than about 1 sec to provide improved effectiveness.

If the compaction delay time is too long, the curing reaction may progress too far prior densification, resulting in reduced performance, such as lower wet strength values. If the compaction delay time is to short, there may not be enough time for the liquid wet-strength agent to adequately spread and distribute into the fibers of the intermediate stratum 40.

In particular arrangements, the wet-strength agent can be cured by subjecting the distributed agent to ambient room temperature (typically about 18–35° C.). As a result, the process and apparatus can be operated with lower cost and greater efficiency. With reference to FIGS. 1 and 2, other configurations of the invention can include a discrete system for curing the wet-strength agent within the absorbent web 26. Various types of curing operations may be employed. Such curing operations include conventional heating, infra-red treatment, other thermal-energy curing operations, chemical curing, radiation curing, electron-beam curing and mechanical-energy curing operations, or the like, as well as combinations thereof. It should be readily apparent that the selection of the particular curing operation will depend upon the type of wet-strength agent incorporated into the absorbent web 26.

In a particular arrangement where a solution or suspension type of liquid agent is employed, the curing operation can include a heating of the absorbent web at a selected temperature for a predetermined period of time, and the heating can be conducted with an operative heating mechanism, such as the representatively shown heating oven 128. Alternatively, the heating mechanism can include an infrared heater, a microwave heater, or the like, as well as combinations thereof.

In particular aspects, the curing system can subject the absorbent web 26 to a curing temperature which is at least a minimum of about 18° C. The curing temperature can alternatively be at least about 30° C., and optionally, can be at least about 80° C. to provide improved performance. In other aspects, the curing temperature can be not more than a maximum of about 200° C. The curing temperature can alternatively be not more than about 150° C., and optionally, can be not more than about 100° C.to provide improved effectiveness.

If the curing temperature is too low, the curing operation may be too slow. This can allow opportunities for the occurrence of unwanted chemical or physical changes. If the curing temperature is too large, the absorbent web can be burnt, discolored or otherwise damaged.

In other aspects, the curing system can subject the absorbent web to an operative curing time, which can be as low as 0.1 sec or as low 0.01 sec. Various techniques, such as infrared curing, microwave curing or electron-beam curing may low curing times may operatively provide such short curing times. Other curing system can provide curing times that are at least a minimum of about 0.1 minutes. The curing time can alternatively be at least about 2 min, and optionally, can be at least about 10 min to provide improved performance. In other aspects, the curing time can be not more than a maximum of about 5000 min. The curing time can alternatively be not more than about 2000 min, and optionally, can be not more than about 1000 min to provide improved effectiveness.

It should be readily appreciated that the curing time will be the time needed to operatively render the intermediate stratum substantially non-dispersible in an aqueous liquid. Accordingly, the curing time will depend upon the particular curing technique that is selected or required for the chosen wet-strength agent material.

The selected curing temperatures and curing times can advantageously help to lower operating costs and increase operating efficiencies. Additionally, the selected parameters can help to better provide the desired levels and combinations of softness, web integrity, wet-strength and liquid-distribution properties.

Figure 3:
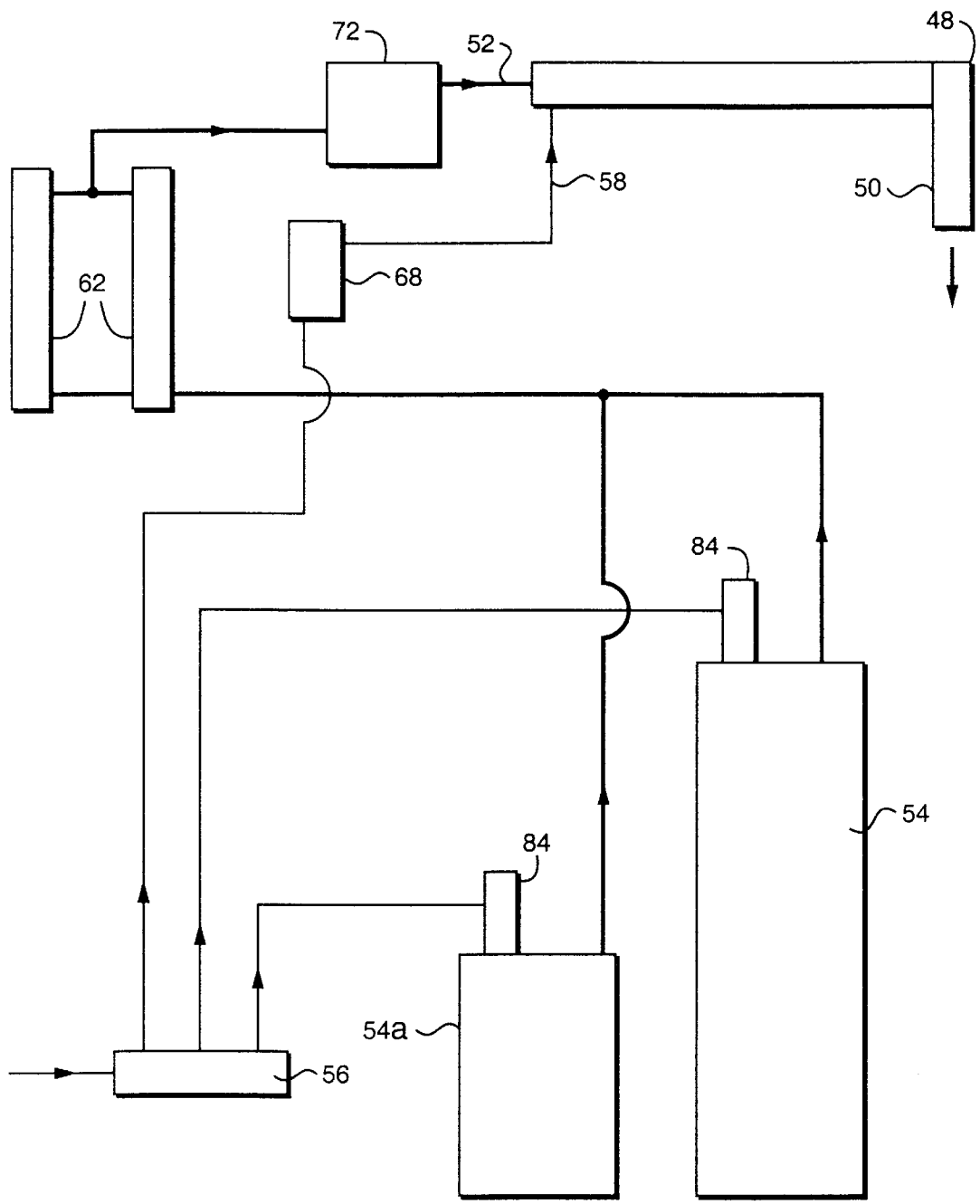
FIG. 3 representatively shows a schematic view of a handling system for supplying the wet-strength agent.

With reference to FIG. 3, a representative system for operatively delivering the liquid, wet-strength agent into the apparatus and process of the invention can include a suitable gas source supply 56 and a suitable agent reservoir or supply source 54. Additionally, the agent system can include a supplemental agent supply source 54a to provide additional operational flexibility, such as a capability to provide more continuous operation.

The gas supply 56 can provide any suitable gas, and in the representatively shown configuration, a convenient gas can be air. The gas supply 56 can operatively provide a pressurized gas which is delivered through suitable conduits, and the gas flow can be controlled with a conventional gas regulator 68. The gas is delivered through a suitable conduit 58 to the spray nozzle assembly 48.

In the representatively shown arrangement, the pressurized gas source 56 can also be employed to deliver the liquid, wet-strength agent 46 from the agent supply source 54. For example, a suitable system of gas regulators 84 can be employed to pressurize the illustrated agent supply tanks 54. The liquid agent 46 is delivered from the supply tanks through suitable conduits, and the delivery of the liquid agent can be operatively controlled by employing conventional systems, such as a system of flow meters 62 and control valve 72. The liquid agent 46 is delivered to the spray nozzle assembly 48 through a suitable conduit 52.

With reference to FIG. 4, the spray nozzle assembly 48 includes an agent spray nozzle 60 and a housing 50. Additionally, the spray assembly 48 can include the agent supply conduit 52 and the gas supply conduit 58. The housing 50 provides a purging gas flow around the agent nozzle 60, and the purging gas flow can substantially prevent an excessive buildup of fibrous material on the agent nozzle 60. Desirably, the housing 50 can be arranged to operatively surround the agent spray nozzle, and the surrounding configuration may be of any desired shape, and may or may not provide a concentric or annular arrangement. The surrounding housing may, for example, be oval, curvilinear, trapezoidal, rectilinear, symmetric or non-symmetric in shape, as well as combinations thereof. Accordingly, the purging gas flow can substantially completely surround the agent nozzle. In the representatively shown arrangement, the housing 50 is positioned substantially concentrically around the agent nozzle 60, and can provide an approximately annular gas flow channel around the agent nozzle. The gas supply conduit 58 delivers an operative supply of gas flow into the housing 50, and the agent supply conduit 52 delivers an operative supply of liquid agent into the agent nozzle 60. Various arrangements of the gas supply conduit 58 and the agent supply conduit 52 would be suitable for constructing the spray nozzle assembly 48. In the representatively shown configuration, for example, the gas conduit 58 is generally coaxially positioned around the agent supply conduit 52.

Figure 4A:
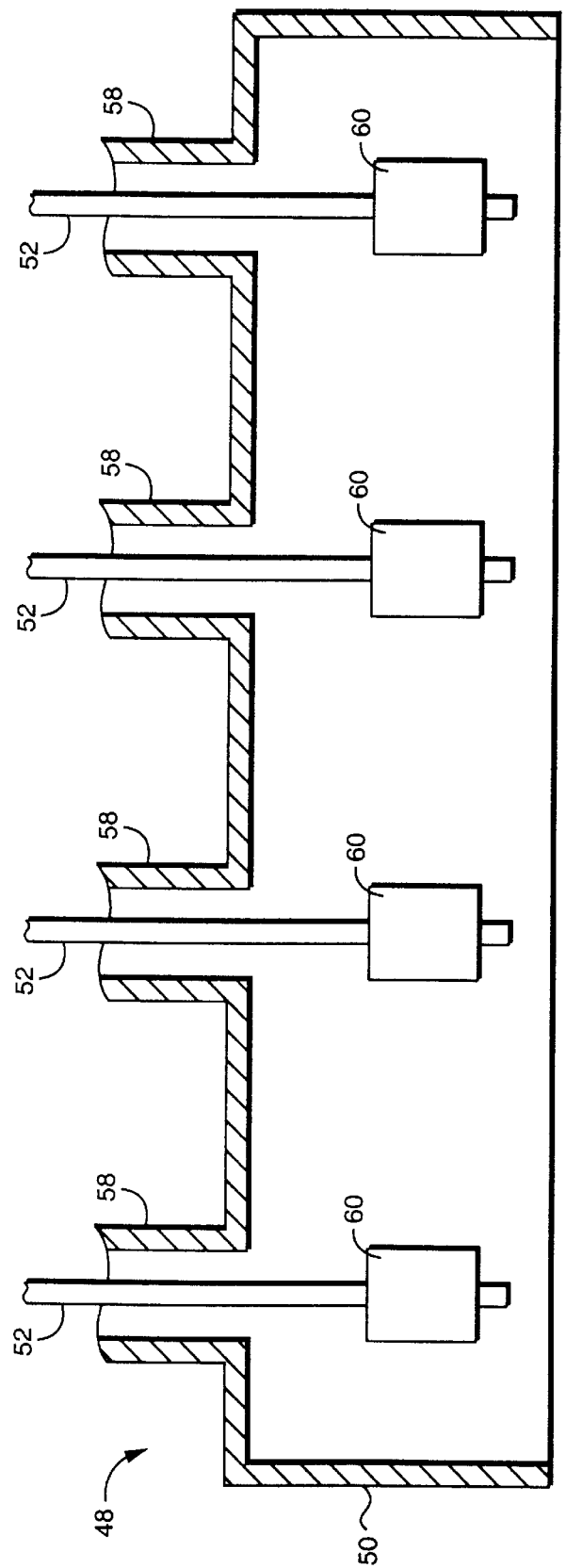
FIG. 4A representatively shows a nozzle system having multiple nozzles that can be employed by the present invention.

In alternative arrangements, the housing 50 may be operatively arranged around a plurality of two or more agent nozzles 60, as representatively shown in FIG. 4A. The nozzles may be aligned or otherwise arrayed along the machine-direction and/or cross-direction, as desired. Each individual nozzle may or may not have an individual, corresponding air conduit 58.

The agent nozzle 60 is preferably recessed into its associated housing 50 by selected inset distance 124. The inset distance may be substantially zero. Desirably, the inset distance can be at least a minimum of about 0.5 mm, and optionally, can be at least about 1 mm to provide improved performance. In other aspects, the inset distance can be not more than a maximum of about 10 mm. The inset distance can alternatively be not more than about 5 mm, and optionally, can be not more than about 2 mm to provide improved effectiveness.

If the nozzle inset distance is too small, the agent distribution nozzle 60 can be excessively susceptible to clogging. If the nozzle inset distance is too large, excessive amounts of the wet-strength agent may be deposited onto the interior surfaces of the housing 50.

It should be readily appreciated that a plurality of two or more agent distribution nozzles 60 and/or spray nozzle assemblies 48 may be employed in the various configurations of the present invention. The plurality of nozzles or nozzle assemblies are operatively arranged to produced the desired distributions and concentrations of wet-strength agent into the appointed fibrous stratum or strata of the absorbent web 26\.

The various aspects and configuration of the invention can advantageously provide the stratified absorbent web 26 with desired combinations of wet-strength and softness. The wet-strength component can, for example, exhibit a selected wet tensile strength and be substantially non-dispersible in an aqueous liquid. The softness component can, for example, remain substantially dispersible in an aqueous liquid. In desired configurations, the absorbent web can be provided with a composite wet-strength which is at least a minimum of about 0.1 grams-force, per 1 gsm (g/m$^2$) of basis weight, per inch of sample width. The wet-strength can alternatively be at least about 0.15 g/gsm/inch, and optionally, can be at least about 0.2 g/gsm/inch to provide improved performance. In other aspects, the wet-strength can be not more than a maximum of about 20 g/gsm/inch. The wet-strength can alternatively be not more than about 5 g/gsm/inch, and optionally, can be not more than about 1 g/gsm/inch to provide improved effectiveness. A suitable technique for determining the wet tensile strength is described in U.S. patent application Ser. No. 09/631494 entitled HIGH-STRENGTH, STABILIZED ABSORBENT ARTICLE by Y. Li et al. which was filed Aug. 3, 2000, the entire disclosure of which is incorporated herein by reference in a manner that is consistent herewith.

In further aspects, the technique of the invention can be arranged to provide the absorbent web with selected levels of dispersibility and non-dispersibility. Desired aspects of the technique of the invention can be arranged to provide the absorbent web with a configuration wherein at least a minimum of about 5 wt % of the absorbent web remains substantially dispersible in an aqueous liquid. Alternatively, at least about 20 wt %, and optionally, at least about 50 wt % of the absorbent web remains substantially dispersible in the aqueous liquid to provide improved performance. In other aspects, not more than a maximum of about 98 wt % of the absorbent web remains substantially dispersible in the aqueous liquid. Alternatively, not more than about 95 wt %, and optionally, not more than about 90 wt % of the absorbent web remains substantially dispersible in the aqueous liquid to provide improved effectiveness. A suitable technique for determining the percentage of the total web that remains substantially dispersible in an aqueous liquid is set forth in U.S. patent application Ser. No. 09/631494 entitled HIGH-STRENGTH, STABILIZED ABSORBENT ARTICLE by Y. Li et al. which was filed Aug. 3, 2000.

The technique of the invention can also be configured to provide an absorbent web which exhibits a selected, remainder basis weight of substantially non-dispersible fibrous material. In particular configurations, the absorbent web can be provided with a substantially non-dispersible, remainder basis weight which is at least about 30 g/m$^2$. The remainder basis weight can alternatively be at least about 100 g/m$^2$, and optionally, can be at least about 150 g/m$^2$ to provided improved performance. A suitable technique for determining the substantially non-dispersible, remainder basis weight of a web is set forth in U.S. patent application Ser. No. 09/631494 entitled HIGH-STRENGTH STABILIZED ABSORBENT ARTICLE by Y. Li et al. which was filed Aug. 3, 2000.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A process for forming an absorbent web, comprising:
    an airlaying of a first fibrous stratum which has a first quantity of absorbent fibers;
    an airlaying of a second fibrous stratum which has a second quantity of absorbent fibers;
    an airlaying of a third, intermediate fibrous stratum which has a third quantity of absorbent fibers, and is integrally formed with said first fibrous stratum and said second fibrous stratum at a location that is interposed between said first fibrous stratum and said second fibrous stratum; and
    a distributing of liquid, wet-strength agent onto said fibers of said intermediate fibrous stratum during said airlaying of said intermediate fibrous stratum to thereby render said intermediate fibrous stratum substantially non-dispersible in liquid.

2. A process as recited in claim 1, wherein said distributing of wet-strength agent includes a spraying of said wet-strength agent onto fibers of said third fibrous stratum during said airlaying of said third fibrous stratum.

3. A process as recited in claim 2, wherein said distributing of wet-strength agent employs a spray assembly having a spray nozzle;
    an outer housing which is arranged to substantially surround said spray nozzle, and extends axially lengthwise beyond a terminal end of said spray nozzle; and
    a gas conduit which delivers a stream of purging gas to said outer housing.

4. A process as recited in claim 1, further comprising a curing of said wet-strength agent.

5. A process as recited in claim 1, further including a compressing together of said fibrous strata prior to said curing of said wet-strength agent.

6. A process as recited in claim 1, wherein said airlaying of said intermediate fibrous stratum superposes said intermediate fibrous stratum onto said first fibrous stratum, and said airlaying of said second fibrous stratum thereafter superposes said second fibrous stratum onto said intermediate fibrous stratum.

7. A process as recited in claim 1, further comprising a moving of a foraminous forming surface through a forming chamber, and an airlaying of said first fibrous stratum on said forming surface.

8. A process as recited in claim 1, further comprising a scarfing of said absorbent web.

9. A process as recited in claim 8, wherein said scarfing is configured to remove a portion of said second fibrous stratum.

10. A process as recited in claim 8, wherein said scarfing is configured to substantially avoid removing material from a stratum which includes said wet strength agent.

11. A process as recited in claim 1, wherein said distributing of said liquid, wet-strength agent onto said fibers of said intermediate fibrous stratum deposits said wet-strength agent substantially continuously along a lengthwise machine-direction of said process.

12. A process as recited in claim 1, wherein said liquid, wet-strength agent has a viscosity of not more than about 50 cP (centipoise).

13. A process as recited in claim 1, wherein said liquid, wet-strength agent provides an amount of agent solids that is at least about 0.05 wt % of the total absorbent web.

14. A process as recited in claim 1, wherein said liquid, wet-strength agent provides an amount of agent solids that is at least about 0.1 wt % of the total absorbent web.

15. A process as recited in claim 14, wherein said wet-strength agent is distributed to provide a dry add-on amount of agent solids which is not more than about 1 wt % of said absorbent web.

16. A process as recited in claim 1, wherein said liquid, wet-strength agent is capable of wetting the fibers in said intermediate fibrous stratum.

17. A process as recited in claim 16, wherein said liquid, wet-strength agent includes an aqueous liquid.

18. A process as recited in claim 1, wherein said wet-strength agent is substantially hydrophilic.

19. A process as recited in claim 1, wherein said wet-strength agent includes a poly(aminoamide)-epocholorohydrin material.

20. A process as recited in claim 1, wherein said wet-strength agent includes a glyoxylated polyacrylamide material.

21. A process as recited in claim 1, wherein said distributing of wet-strength agent substantially avoids distributing wet-strength agent into said first fibrous stratum.

22. A process as recited in claim 21, wherein said distributing of wet-strength agent substantially avoids distributing wet-strength into said second fibrous stratum.

23. A process as recited in claim 1, further including a distributing of a quantity of superabsorbent material in said absorbent web.

24. A process as recited in claim 1, further comprising a densifying of said absorbent web to a composite density of at least about 0.05 g/cm$^3$.

25. A process as recited in claim 24, further comprising a densifying of said absorbent web to a composite density of not more than about 0.15 g/cm$^3$.

26. A process as recited in claim 1, wherein the process is arranged to configure said absorbent web with a substantially non-dispersible, remainder basis weight which is at least about 50 g/m$^2$.

27. A process as recited in claim 1, wherein the process provides said absorbent web with a configuration in which at least about 20 wt % of the absorbent web remains substantially dispersible in an aqueous liquid.

28. A process as recited in claim 1, wherein the process provides said absorbent web with a composite wet-strength which is at least a minimum of about 0.1 grams-force, per 1 gsm (g/m$^2$) of basis weight, per inch of sample width.

29. An apparatus for forming an absorbent web, comprising:
   a forming surface;
   a fiber source which can supply fibers for airlaying onto said forming surface to provide
      a first fibrous stratum having a first quantity of absorbent fibers,
      a second fibrous stratum having a second quantity of absorbent fibers, and
      an intermediate fibrous stratum having a third quantity of absorbent fibers, said intermediate fibrous stratum integrally formed with said first fibrous stratum and said second fibrous stratum at a location that is interposed between said first fibrous stratum and said second fibrous stratum; and
   a nozzle which can distribute a liquid, wet-strength agent onto said fibers of said intermediate fibrous stratum during said airlaying of said intermediate fibrous stratum to thereby render said intermediate fibrous stratum substantially non-dispersible in liquid.

30. An apparatus as recited in claim 29, further comprising:
   a forming chamber; and
   a transporter which can move said forming surface through said forming chamber.

* * * * *